United States Patent [19]
Chen et al.

[11] Patent Number: 6,159,493
[45] Date of Patent: Dec. 12, 2000

[54] FORMULATION AND METHOD OF MANUFACTURING AN ACNE EXTRACTION PATCH

[75] Inventors: Shu-Juan Chen; Chao-Wei Liao, both of Hsinchu; Chien-Hsin D. Cheng, Hsinchu Hsien, all of Taiwan

[73] Assignee: Caleb Pharmaceuticals, Inc., Hsinchu, Taiwan

[21] Appl. No.: 09/021,965

[22] Filed: Feb. 11, 1998

[30] Foreign Application Priority Data

Nov. 28, 1997 [TW] Taiwan ................................. 86117919

[51] Int. Cl.[7] ...................................................... A61K 9/70
[52] U.S. Cl. ........................ 424/443; 424/78.03; 424/401; 514/859
[58] Field of Search ................................ 424/443, 78.03, 424/401; 514/859

[56] References Cited

U.S. PATENT DOCUMENTS

| | | | |
|---|---|---|---|
| 4,699,146 | 10/1987 | Sieverding | 128/640 |
| 4,920,158 | 4/1990 | Murray | 523/111 |
| 5,456,745 | 10/1995 | Roreger | 106/128 |
| 5,512,277 | 4/1996 | Uemura | 424/78.03 |
| 5,567,428 | 10/1996 | Hughes | 424/401 |
| 5,874,074 | 2/1999 | Smith | 424/78.02 |

*Primary Examiner*—Shelley A. Dodson
*Assistant Examiner*—Michael A. Williamson
*Attorney, Agent, or Firm*—Merchant & Gould P.C.

[57] ABSTRACT

A formulation and a method for manufacturing an acne extraction patch. Water is added into polyvinyl alcohol and polyvinyl pyrrolidone to form an polymer solution. An adequate excipient is further added to form an optimal formulation. The formulation is coated directly onto the hydrophilic nonwovens or the nonwovens are placed over the release liner after coating the release liner with silicon coating. After the steps described above, the nonwovens are put into the dry oven for a two-step drying method at 55–90° C., and 80–95° C. A die-cut and package machine is used to cut an adequate patch. The patch is moistened with water and applied to the face or nose. The water solution of the formulation penetrates into the hair follicles or sebaceous glands. The lug of acne sticks to the polymer patch as the water evaporates. The acne is extracted from the hair follicle as the patch is removed.

18 Claims, No Drawings

6,159,493

FORMULATION AND METHOD OF MANUFACTURING AN ACNE EXTRACTION PATCH

CROSS-REFERENCE TO RELATED APPLICATION

This application claims priority benefit of Taiwan application Serial no. 86117919, filed Nov. 28, 1997, the full disclosure of which is incorporated herein by reference.

BACKGROUND OF THE INVENTION

1. Field of the Invention

The invention relates to an acne extraction patch, and more particularly to a formulation for an acne extraction patch.

2. Description of the Related Art

People with oleaginous skin normally have oleaginous face problems, such as shadding of cosmetics, pimples, acne, etc. Skin maintenance already on the market not only decrease but inhibit steaeoexcretion, however, it is not really available so much to solve the cosmetic problem of acne as it is to inhibit stereoexcretion. In order to extract acne from the face, it is a better and direct treatment to extract acne locally. Commercially, available masks are used presently to extract acne.

Polymers like polyvinyl alcohol (PVA) and polyvinyl pyrrolidone (PVP) are mixed with water to form a polymer solution which is smeared on the face or nose. The polymer solution penetrates hair follicles and sebaceous glands. The water molecule around PVA and PVA polymer solution is induced far from the surface of the skin because of the hydrophobic of skin, which makes the viscosity of the polymer solution near the skin increase rapidly. The lug of acne inside the hair follicles or sebaceous glands is surrounded by the polymer substrate. After half hour of drying at general temperature, the water evaporates and the PVA and PVP polymer solution becomes hard. The lug of acne sticks to the polymer patch, and is extracted from the hair follicles or sebaceous glands as the patch is removed.

SUMMARY OF THE INVENTION

It is therefore an object of the invention to provide a formulation of an acne extraction patch, to completely solve the problem of acne for people with oleaginous skin.

It is another object of the invention to provide an optimal method of manufacturing a patch which can extract acne. This method will be maximally economical and convenient.

To achieve these objects and advantages, and in accordance with the purpose of the invention, as embodied and broadly described herein, the invention is directed towards an optimal formulation and method of manufacturing an acne extraction patch. Polyvinyl alcohol is solubilized into water to form a polyvinyl alcohol solution. Polyvinyl pyrrolidone is added into the polyvinyl alcohol solution, and an adequate excipient is further added into the polyvinyl alcohol solution to form an optimal formulation. The formulation is coated directly on the hydrophilic nonwovens or addition of the nonwovens after coating the release liner with silicone coating. After the steps described above, the nonwovens is put into the dry oven for a two-step drying method. Step one is at 55–90° C., and step two is at 80–95° C. A die-cut and package machine is used to cut an adequate patch. The patch is moistened with water and adhered to the face or nose. The water solution of the formulation penetrates the hair follicles and sebaceous glands. The lug of the acne is adhered to the polymer patch after the water evaporates. The acne is extracted from the hair follicles as the patch is removed. This invention discloses an optimal formulation and a method of manufacturing for an extraction acne patch, so that the treatment is more effective and the method is more economical and convenient.

It is to be understood that both the foregoing general description and the following detailed description are exemplary and explanatory only and are not restrictive of the invention, as claimed.

DESCRIPTION OF THE PREFERRED EMBODIMENTS

The polyvinyl alcohol of the first main ingredient, the polyvinyl pyrrolidone of the second main ingredient and the water molecule compound to form a polymer solution. The first main ingredient is 0.5%–5% PVA. The second main ingredient is 1%–20% PVP. The excipient is added to make an optimal formulation and the acne extraction is formed on a nonwovens coating.

The excipient makes the first main ingredient and the second ingredient react and the excipient includes several components, vinyl pyrrolidone/vinyl acetatecopolymer (PVPNA Copolymer) as thickener, methyl vinyl ether/maleic anhydride copolymer (PVM/MA Copolymer) as tackifier, glyceryl behenate as adhesive, triethyl citrate as buffer, glycerin as softener, polyoxyethylene sorbitan monooleate as surfactant, musk oil as essence, and imidazolidinyl urea (Unicide) as antiseptic.

The preferred concentration of the excipient's ingredients are as follows: 0.1%–10% PVP/VA as thickener, 0.5%–10% PVM/MA as tackifier, 0.1%–3% glyceryl behenate as adhesive, 0.5%–10% triethyl citrate as buffer, 0.1%–9% glycerin as softener, 0.1%–10% polyoxyethylene sorbitan monooleate as surfactant, 0.1%–0.2% musk oil as essence, and 0.1%–0.2% of imidazolidinyl urea as antiseptic.

These are the steps to make the optimal formulation for an acne extraction patch. There are two methods in the process of the invention. In the first method, the formulation for the acne extraction patch is coated onto the release liner with silicone coating while it is on the roll coaster of the coating machine. When the formulation is thoroughly absorbed by the release liner, the nonwovens is placed over the coating layer to make the formulation transfer to the nonwovens. Then the film roll is placed in the dry oven and dried in a two-step drying method, at a temperature of 55–90° C., and 80–95° C. The film roll is cut into patches using the die-cut and package machine. In the second method, the formulation is coated directly onto the nonwovens and put into the dry oven. Then the film roll is dried with a two-step drying method, at temperatures of 55–90° C., and 80–95° C.

Other embodiment of the invention will appear to those skilled in the art from consideration of the specification and practice of the invention disclosed herein. It is intended that the specification and examples to be considered as exemplary only, with a true scope and spirit of the invention being indicated by the following claims.

What is claimed is:

1. A formulation for an acne extraction patch, comprising:
    a polyvinyl alcohol solution, wherein the polyvinyl alcohol has a concentration range of between about 0.5% and 5%;
    a polyvinyl pyrrolidone, wherein the polyvinyl pyrrolidone has a concentration range of between about 1% and 20%; and
    an adequate excipient.

2. A The formulation according to claim 1, wherein the excipient comprises a thickener, a tackifier, an adhesive, a buffer, a softener, a surfactant, as essence and an antisetic.

3. The formulation according to claim 2, wherein the thickener includes vinyl pyrrolidone/vinyl acetate copolymer.

4. The formulation according to claim 3, wherein the concentration of the copolymer is in the range of between about 0.1% and 10%.

5. The formulation according to claim 2, wherein the tackifier includes methyl vinyl ether/maleic anhydride copolymer.

6. The formulation according to claim 2, wherein the concentration of the adhesive is in the range of between about 0.5% and 10%.

7. The formulation according to claim 2, wherein the adhesive includes glyceryl behenate.

8. The formulation according to claim 2, wherein the concentration of the adhesive is in the range of between about 0.1% and 3%.

9. The formulation according to claim 2, wherein the buffer includes triethyl citrate.

10. The formulation according to claim 2, wherein the concentration of the buffer is in the range of between about 0.5% and 10%.

11. The formulation according to claim 2, wherein the softener includes glycerin.

12. The formulation according to claim 2, wherein the concentration of the softener is in the range of between about 0.1% and 9%.

13. The formulation according to claim 2, wherein the surfactant includes polyoxyethylene sorbitan monooleate.

14. The formulation according to claim 2, wherein the concentration of the surfactant is in the range of between about 0.1% and 10%.

15. The formulation according to claim 2, wherein the essence includes musk oil.

16. The formulation according to claim 2, wherein the concentration of the essence is in the range of between about 0.1% and 0.2%.

17. The formulation according to claim 2, wherein the antiseptic includes imidazolidinyl.

18. The formulation according to claim 2, wherein the concentration of the antiseptic is in the range of between about 0.1% and 0.2%.

* * * * *